(12) United States Patent
Yee et al.

(10) Patent No.: US 11,284,991 B2
(45) Date of Patent: Mar. 29, 2022

(54) SYNTHETIC POLYMERIC IMPLANTABLE ARTIFICIAL CORNEA DEVICE INCORPORATING NANOPATTERNS

(71) Applicant: The Regents of the University of California, Oakland, CA (US)

(72) Inventors: Albert Yee, Irvine, CA (US); Marjan Farid, Irvine, CA (US); Roger Steinert, Irvine, CA (US); Elena Liang, Irvine, CA (US); Mary Nora Dickson, Costa Mesa, CA (US)

(73) Assignee: The Regents of the University of California, Oakland, CA (US)

( * ) Notice: Subject to any disclaimer, the term of this patent is extended or adjusted under 35 U.S.C. 154(b) by 533 days.

(21) Appl. No.: 16/083,746

(22) PCT Filed: Mar. 10, 2017

(86) PCT No.: PCT/US2017/021908
§ 371 (c)(1),
(2) Date: Sep. 10, 2018

(87) PCT Pub. No.: WO2017/156460
PCT Pub. Date: Sep. 14, 2017

(65) Prior Publication Data
US 2020/0163753 A1 May 28, 2020

Related U.S. Application Data

(60) Provisional application No. 62/307,304, filed on Mar. 11, 2016.

(51) Int. Cl.
*A61F 2/14* (2006.01)
*A61L 27/34* (2006.01)
*A61L 27/50* (2006.01)

(52) U.S. Cl.
CPC ............ *A61F 2/142* (2013.01); *A61L 27/34* (2013.01); *A61L 27/50* (2013.01);
(Continued)

(58) Field of Classification Search
CPC ........ A61F 2/142; A61F 2/145; A61F 2/1451; A61F 2/15; A61F 2/147; A61F 2/1453;
(Continued)

(56) References Cited

U.S. PATENT DOCUMENTS 6,106,552 A   8/2000 Lacombe et al.
7,229,685 B2* 6/2007 Full ........................... C09J 5/00
                                           428/343

(Continued)

FOREIGN PATENT DOCUMENTS

WO   2013172794 A1   11/2013
WO   2015055656 A1   4/2015
(Continued)

OTHER PUBLICATIONS

International Preliminary Report on Patentability for International Application PCT/US2017/021908, Report dated Sep. 11, 2018, dated Sep. 20, 2018, 9 pgs.
(Continued)

*Primary Examiner* — Jennifer Dieterle
*Assistant Examiner* — Tiffany P Shipmon
(74) *Attorney, Agent, or Firm* — KPPB LLP

(57) ABSTRACT

In various embodiments, disclosed herein is an artificial cornea, comprising an optic zone that is similar in thickness to a natural cornea and a peripheral skirt having a thickness less than the thickness of the optic zone, where the surfaces of the optic zone and peripheral skirt comprise one or more microstructures or nanostructures. In various embodiments, further disclosed herein are methods of manufacturing nanostructures on an artificial cornea, as well as treating a disease
(Continued)

by providing an artificial cornea having one or more microstructures and/or nanostructures.

30 Claims, 2 Drawing Sheets

(52) U.S. Cl.
CPC ....... *A61L 2400/12* (2013.01); *A61L 2400/18* (2013.01); *A61L 2430/16* (2013.01)

(58) Field of Classification Search
CPC .......... A61L 27/34; A61L 27/50; A61L 27/52; A61L 2400/12; A61L 2400/18; A61L 2430/16

See application file for complete search history.

(56) References Cited

U.S. PATENT DOCUMENTS

| | | | |
|---|---|---|---|
| 10,828,394 B2 | 11/2020 | Yee et al. | |
| 11,086,049 B2 | 8/2021 | Yee et al. | |
| 2003/0175325 A1 | 9/2003 | Chatelier et al. | |
| 2007/0168025 A1* | 7/2007 | Darougar | A61F 2/142 623/5.14 |
| 2007/0227428 A1 | 10/2007 | Brennan et al. | |
| 2008/0317982 A1 | 12/2008 | Hecht et al. | |
| 2009/0194913 A1 | 8/2009 | Chang et al. | |
| 2009/0266418 A1 | 10/2009 | Hu et al. | |
| 2010/0036488 A1* | 2/2010 | de Juan, Jr. | A61F 2/142 623/5.16 |
| 2010/0239637 A1 | 9/2010 | Ciolino et al. | |
| 2011/0125260 A1* | 5/2011 | Shen | A61L 27/52 623/5.16 |
| 2011/0135814 A1* | 6/2011 | Miyauchi | C12M 25/06 427/123 |
| 2011/0160851 A1* | 6/2011 | Mueller-Lierheim | A61F 2/142 623/5.13 |
| 2011/0208300 A1* | 8/2011 | de Juan, Jr. | A61F 2/142 623/5.14 |
| 2012/0040461 A1 | 2/2012 | Beachley et al. | |
| 2013/0059113 A1 | 3/2013 | Hatton et al. | |
| 2013/0244889 A1* | 9/2013 | Yim | G03F 7/0002 506/7 |
| 2014/0305904 A1 | 10/2014 | Lan | |
| 2015/0104522 A1 | 4/2015 | Xu | |
| 2015/0104622 A1 | 4/2015 | Chong et al. | |
| 2015/0273755 A1 | 10/2015 | Yee et al. | |
| 2017/0293158 A1 | 10/2017 | Markus et al. | |
| 2019/0075789 A1 | 3/2019 | Yee et al. | |
| 2019/0076573 A1 | 3/2019 | Yee et al. | |
| 2019/0101669 A1 | 4/2019 | Yee et al. | |

FOREIGN PATENT DOCUMENTS

| | | | |
|---|---|---|---|
| WO | 2017156460 A1 | 9/2017 | |
| WO | 2017160658 A1 | 9/2017 | |
| WO | 2017156460 A8 | 5/2018 | |

OTHER PUBLICATIONS

International Preliminary Report on Patentability for International Application PCT/US2017/021926, Report dated Sep. 18, 2018, dated Sep. 27, 2018, 7 pgs.

International Search Report and Written Opinion for International Application No. PCT/US2017/021908, Search completed Jun. 23, 2017, dated Jul. 7, 2017, 12 pgs.

International Search Report and Written Opinion for International Application No. PCT/US2017/021926, Search completed Apr. 25, 2017, dated Jun. 1, 2017, 8 pgs.

Sony Provisional Patent Application No. 60,409,675, filed Sep. 9, 2002, 144 pgs.

Banerjee et al., "Antifouling Coatings: Recent Developments in the Design of Surfaces That Prevent Fouling by Proteins, Bacteria, and Marine Organisms.", Advanced Materials, Feb. 11, 2011, vol. 23 Issue 6, pp. 690-715.

Chung et al., "Impact of engineered surface microtopography on biofilm formation of *Staphylococcus aureus*", Biointerphases, Jun. 2007, vol. 2, Issue 2, pp. 89-94.

Hasan et al. "Selective bactericidal activity of nanopatterned superhydrophobic cicada Psaltoda claripennis wing surfaces", Appl Microbiol Biotechnol, 2013, vol. 97, pp. 9257-9262.

Kirschner et al. "Bio-Inspired Antifouling Strategies, Annual Review of Materials Research", 2012, vol. 42, pp. 211-229.

Kopplmayr et al. "Nanoimprint Lithography on curved surfaces prepared by fused deposition modelling", Surface Topography: Metrology and Properties. Jun. 2015, vol. 3, No. 2, 024003, 12 pgs.

Liu et al. "Bio-Inspired Design of Multiscale Structures For Function Integration, Nano Today", Apr. 2011, vol. 6 issue 2, pp. 155-175.

Lvanova et al. "Natural Bactericidal Surfaces: Mechanical Rupture of Pseudomonas aeruginosa Cells by Cicada Wings", Small, Aug. 20, 2012, vol. 8, Issue16, pp. 2489-2494.

Pogodin et al. "Biophysical Model of Bacterial Cell Interactions with Nanopatterned Cicada Wing Surfaces", Biophysical Journal vol. 104, Issue 4, 2013 pp. 835-840.

Sun et al. "Wetting properties on nanostructured surfaces of cicada wings", The Journal of Experimental Biology Oct. 1, 2009, vol. 212, Issue 19, pp. 3148-3155.

Yao et al. "Atomic Force Microscopy and Theoretical Considerations of Surface Properties and Turgor Pressures of Bacteria", Colloids and Surfaces B: Biointerfaces 2002, vol. 23, pp. 213-230.

Zhang et al. "Cicada Wings: A Stamp from Nature for Nanoimprint Lithography", Small Dec. 2006, vol. 2 Issue 12, pp. 1440-1443.

Deodhar et al., "Conserved Activity of Reassociated Homotetrameric Protein Subunits Released from Mesoporous Silica Nanoparticles", Langmuir, 2018, Published Dec. 12, 2017, vol. 34, pp. 228-233, doi: 10.1021/acs.langmuir.7b03310.

Gause et al., "Mechanistic modeling of ophthalmic drug delivery to the anterior chamber by eye drops and contact lenses", Advances in Colloid and Interface Science, 2016, Available Online Aug. 14, 2015, vol. 233, pp. 139-154 doi: 10.1016/j.cis.2015.08.002.

Tang et al., "Mesoporous Silica Nanoparticles: Synthesis, Biocompatibility and Drug Delivery", Advanced Materials, Feb. 29, 2012, vol. 24, No. 12, pp. 1504-1534, doi: 10.1002/adma.201104763.

Zhang et al., "Surface Modification of Polymethyl Methacrylate Intraocular Lenses by Plasma for Improvement of Antithrombogenicity And Transmittance", Applied Surface Science, vol. 255, pp. 6840-6845, Year (2009).

* cited by examiner

SYNTHETIC POLYMERIC IMPLANTABLE ARTIFICIAL CORNEA DEVICE INCORPORATING NANOPATTERNS

CROSS REFERENCE TO RELATED APPLICATIONS

This application is a National Phase of International Application No. PCT/US2017/021908, filed Mar. 10, 2017, which designated the U.S. and that International Application was published under PCT Article 21(2) in English. This application also includes a claim of priority under 35 U.S.C. 0 119(e) to U.S. Provisional Application No. 62/307,304, filed Mar. 11, 2016, the entirety of which is hereby incorporated by reference.

FIELD OF THE INVENTION

The present disclosure is in the medical and biomedical field, specifically implantable medical devices.

BACKGROUND OF THE DISCLOSURE

Corneal blindness accounts for up to 50% of blindness. An artificial cornea is required in cases where a donor cornea is unavailable or is contraindicated. Currently available artificial cornea devices on the market, such as the Boston Keratoprosthesis for example, consists of poly(methyl methacrylate) front and back plates, sandwiching a donor cornea. In cases where a donor cornea is unavailable, there is no good substitute. Currently available artificial corneas are made of two materials, a clear optic zone, and a spongy, porous, or gel-like skirt. The junction between the two materials is mechanically weak and is prone to failure. Additionally, this mismatch creates a site for inflammation or for bacterial infection. Indeed in the Boston Keratoprosthesis, stromal melt is often observed at the interface between the polymer portion and the donor cornea. As such, patients with artificial corneal prosthetics often require administration of antibiotics for the lifetime of the device.

Therefore there exists a need for a new artificial cornea that is easy to implant, durable, and has a decreased risk of microbial infections.

SUMMARY OF THE DISCLOSURE

In various embodiments, disclosed herein is an artificial cornea, comprising: an optic zone, having a thickness between 50 μm and 2 mm; and a peripheral skirt, having a thickness less than the thickness of the optic zone; and wherein the surfaces of the optic zone and peripheral skirt comprise one or more microstructures or nanostructures. In one embodiment, the peripheral skirt is tapered and is sutured into a host corneal tissue. In one embodiment, the artificial cornea has one continuous curvature on the posterior side. In one embodiment, the artificial cornea is manufactured from a biocompatible material. In one embodiment, the artificial cornea is manufactured from a transparent plastic material. In one embodiment, the transparent plastic material is poly(methyl methacrylate). In one embodiment, the artificial cornea further comprises a coating of metal oxides, fibronectin, laminin, collagen, and/or silane. In one embodiment, the optic zone and the peripheral skirt has the same radius of curvature. In one embodiment, the optic zone and the peripheral skirt has different radius of curvature. In one embodiment, the artificial cornea has a diameter between 8 mm and 11 mm. In one embodiment, the optic zone has a diameter between 3 mm and 6 mm. In one embodiment, the peripheral skirt comprises one or more suture openings. In one embodiment, the number of suture openings is between 4 and 16. In one embodiment, the suture openings have a diameter between 0.5 mm and 2 mm. In one embodiment, the microstructures or nanostructures on the peripheral skirt comprise micrometer wide lines or nanometer wide lines. In one embodiment, the micrometer wide lines or nanometer wide lines in the peripheral skirt promotes host cell adhesion. In one embodiment, the nanometer wide lines are between 200 nm and 2000 nm in width. In one embodiment, the microstructures or nanostructures are on the anterior surface of the peripheral skirt. In one embodiment, the microstructures or nanostructures are on the anterior and posterior surfaces of the peripheral skirt. In one embodiment, the micrometer wide lines or nanometer wide lines may orient in any direction on the anterior posterior surfaces of the prosthesis. In one embodiment, the microstructures or nanostructures on the optic zone comprise micropillars or nanopillars. In one embodiment, the nanopillars are between 20 nm to 200 nm in diameter. In one embodiment, the nanopillars are tapered at the tip and have a diameter between 10 nm and 200 nm. In one embodiment, the micropillars or nanopillars have a round, curved, or rectilinear in cross-sectional shape. In one embodiment, the microstructures or nanostructures are on the anterior surface of the optic zone. In one embodiment, the microstructures or nanostructures are on the anterior and posterior surfaces of the optic zone. In one embodiment, the microstructures or nanostructures on the optic zone prevents formation of retroprosthetic membrane and infectious keratitis. In one embodiment, the microstructures or nanostructures on the optic zone deters host cell adhesion. In one embodiment, the microstructures or nanostructures on the optic zone has antimicrobial or microbicidal properties. In one embodiment, the microstructures or nanostructures are fabricated from the same polymer as the artificial cornea device.

In various embodiments, disclosed herein is a method of manufacturing nanostructures on an artificial cornea comprising: providing an artificial cornea comprising an optic zone and a peripheral skirt; providing a planar master mold with nano features; fabricating an elastomeric replicate mold of the master mold; deforming the elastomeric negative mold into the desired curved architecture; and manufacturing nanostructures on the artificial cornea by using the curved elastomeric negative mold to mold nanostructures on the artificial cornea. In one embodiment, the nanostructures on the peripheral skirt comprise nanometer wide lines. In one embodiment, the nanometer wide lines in the peripheral skirt promotes host cell adhesion. In one embodiment, the nanostructures on the optic zone comprise nanopillars. In one embodiment, the nanostructures on the optic zone prevents formation of retroprosthetic membrane and/or infectious keratitis. In one embodiment, the nanostructures on the optic zone deters host cell adhesion. In one embodiment, the nanostructures on the optic zone has antimicrobial or microbicidal properties.

In various embodiments, disclosed herein is a method of treating a disease comprising: providing an artificial cornea having microstructures or nanostructures; and treating a disease with the artificial cornea. In one embodiment, the artificial cornea comprises: an optic zone, having a thickness between 50 μm and 2 mm; and a peripheral skirt, having a thickness less than the thickness of the optic zone; wherein the surface of the optic zone comprises nanometer wide lines that promotes host cell adhesion; and wherein the surface of the peripheral skirt comprises nanopillars that deter host cell adhesion and provides antimicrobial properties to the artificial cornea. In one embodiment, the disease is a corneal disease.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
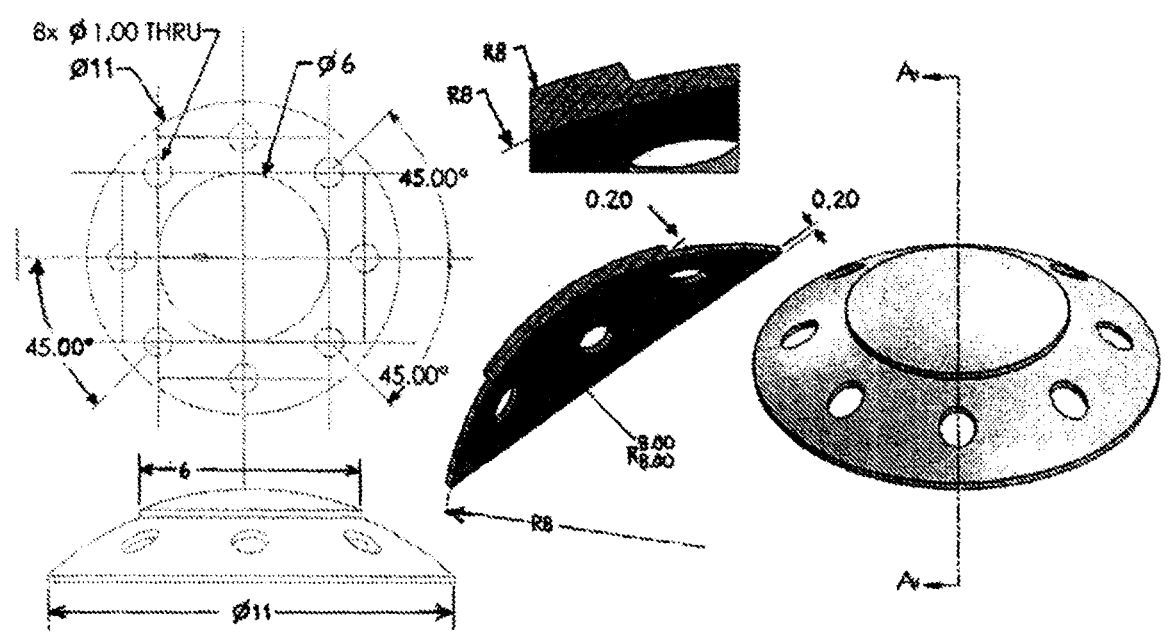
FIG. 1 illustrates, in accordance with embodiments herein, an artificial cornea made from poly-methylmethacrylate (PMMA), with nanostructures.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "nanostructure(s)," as used herein, refers to structures having a size between molecular and microscopic structures. Typically, such structures have at least one dimension on the nanoscale, e.g., between about 1 nm and about 999 nm. The nanostructures can be configured so as to also include one or more of the following: (1) a nano surface having one dimension on the nanoscale, for example, a surface thickness between 1 nm and 999 nm; (2) a nanopillar or nanotube having two dimensions on the nanoscale, for example, a diameter and length each between 1 nm and 999 nm; and/or (3) a nanoparticle having three dimensions on the nanoscale, for example, the three spatial dimensions of the nanoparticle being between 1 nm and 999 nm. In one embodiment, the term nanopillar further refers to vertically oriented elongate structures, which may be straight, winding, zigzag, or crooked.

The term "microstructure(s)," as used herein, refers to structures having at least one dimension on the microscale, e.g., between about 1 µm and about 999 µm. The microstructures can be configured so as to include one or more of the following: (1) a micro surface having one dimension on the microscale, for example, a surface thickness between 1 µm and 999 µm; (2) a micropillar or microtube having two dimensions on the microscale, for example, a diameter and length each between 1 µm and 999 µm; and/or (3) a microparticle having three dimensions on the microscale, for example, the three spatial dimensions of the nanoparticle being between 1 µm and 999 µm. In one embodiment, the term micropillar further refers to vertically oriented elongate structures, which may be straight, winding, zigzag, or crooked.

The term "nanometer wide lines," as used herein, refers to nanostructures in the shape of a line wherein the diameter of the line is between 1 nm and 999 nm. The term "micrometer wide lines," as used herein, refers to microstructures in the shape of a line wherein the diameter of the line is between 1 µm and 999 µm. The lines may be straight, winding, zigzag, or crooked.

The term "touch device," as used herein, refers to a device that can be touched, or a device that is responsive to a touch. Examples of touch devices that are responsive to a touch include, but not limited to, a keypad, touch screen, and/or one or more buttons to allow a user to enter some form of input.

As known to a skilled artisan in the art, the term "optic zone" refers to the center part of the artificial cornea, which functions as the optical part of the artificial cornea covering all or part of the anterior chamber of the eye.

As known to a skilled artisan in the art, the term "peripheral skirt" refers to the part of the artificial cornea that is located around and substantially surrounding perimeter of the optic zone. In one embodiment, the peripheral skirt traverses the anterior sclera beneath the conjunctiva-tenon complex.

As described herein, and in accordance with the various embodiments, the inventors have created an implantable artificial cornea, wherein the surfaces of the artificial cornea comprise one or more microstructures or nanostructures, and wherein the microstructures or nanostructures are capable of possessing antimicrobial or microbicidal properties. In accordance with the various embodiments, described herein is a completely synthetic, implantable artificial cornea device with nanopatterns to control surface functions.

In accordance with various embodiments, disclosed herein is an artificial cornea comprising (a) an optic zone that is similar in thickness to a natural cornea; and (b) a peripheral skirt having a thickness less than the thickness of the optic zone; and wherein the surfaces of the optic zone and peripheral skirt comprise one or more microstructures or nanostructures. The term "similar" in thickness, as used herein, refers to a thickness that is within 50% of each other, or more preferably within 25% of each other, or most preferably within 10% of each other. Thus the term optic zone that is similar in thickness to a natural cornea would refer to an optic zone whose thickness is +/−50% of the thickness of natural cornea, or more preferably +/−25% of the thickness of natural cornea, or most preferably +/−10% of the thickness of natural cornea. In one embodiment, the thickness of the optic zone is 50 µm-2 mm, or more preferably 75 µm-1.5 mm, or more preferably 100 µm-1000 µm, or more preferably 200 µm-800 µm, or more preferably 300 µm-700 µm, or most preferably 400 µm-600 µm. One embodiment of the artificial cornea is described in FIG. 1 herein. In some embodiments, the peripheral skirt is tapered such that it is capable of being sutured into a pocket in the host corneal tissue. In some embodiments, the peripheral skirt has suture openings. In some embodiments, the artificial cornea is made in one piece. In some embodiments, the artificial cornea has one continuous curvature on the posterior side. In some embodiments, the optic zone protrudes into the eye in the posterior direction. In some embodiments, the artificial cornea is manufactured from a transparent plastic material. In some embodiments, the transparent plastic material is poly (methyl methacrylate). In some embodiments, the transparent plastic material is an FDA approved material. In some embodiments, the artificial cornea is manufactured from a biocompatible material. In some embodiments, the optic zone and the peripheral skirt has the same radius of curvature. In some embodiments, the optic zone and the peripheral skirt has different radius of curvature. In some embodiments, the cornea device has a diameter between 8 mm and 11 mm. In some embodiments, the optic zone has a diameter between 3 mm and 6 mm. In some embodiments, the peripheral skirt comprises suture openings. In some embodiments, the number of suture openings is between 4 and 16. In some embodiments, each of the suture openings has a diameter between 0.5 mm and 2 mm.

In various embodiments, the microstructures or nanostructures on the peripheral skirt of the artificial cornea comprise micrometer wide lines or nanometer wide lines. In one embodiment, the micrometer wide lines or nanometer wide lines in the peripheral skirt promotes host cell adhesion. In some embodiments, the nanometer wide lines are between 200 nm and 2000 nm in width. In some embodiments, the peripheral skirt comprises a coating comprising metal oxides, fibronectin, laminin, collagen or silane. In some embodiments, the microstructures or nanostructures are on the anterior surface of the peripheral skirt. In some embodiments, the microstructures or nanostructures are on the anterior and posterior surfaces of the peripheral skirt. In some embodiments, the micrometer wide lines or nanometer wide lines may orient in any direction on the anterior and posterior surfaces of the prosthesis.

In various embodiments, the microstructures or nanostructures on the optic zone of the artificial cornea comprise micropillars or nanopillars. In some embodiments, the microstructures or nanostructures are on the anterior surface of the optic zone. In some embodiments, the micro-structures or nanostructures are on the anterior and posterior surfaces of the optic zone. In one embodiment, the microstructures or nanostructures on the optic zone prevents formation of retroprosthetic membrane and infectious keratitis. In some embodiments, the microstructures or nanostructures on the optic zone deters host cell adhesion. In some embodiments, the microstructures or nanostructures on the optic zone has antimicrobial or microbicidal properties. In some embodiments, the optic zone comprises a coating, comprising metal oxides, fibronectin, laminin, collagen or silane. In some embodiments, the nanopillars are between 20 nm to 200 nm in diameter. In some embodiments, the nano-pillars are tapered at the tip and has a diameter between 10 nm and 200 nm. In some embodiments, the micropillars or nanopillars have a round, curved, or rectilinear in cross-sectional shape. In some embodiments, the microstructures or nanostructures are fabricated from the same polymer as the artificial cornea device.

In one embodiment, the micrometer wide lines or nanometer wide lines are not on the optic zone of the artificial cornea.

In various embodiments, disclosed herein is a method of making an artificial cornea comprising: (a) providing a planar master mold with micro or nano features; (b) fabricating an elastomeric replicate mold (elastomeric negative mold) of the master mold; (c) deforming the elastomeric negative mold into the desired curved architecture; and (d) using the curved elastomeric negative mold to mold a microstructure or nanostructure structure on the artificial cornea.

In various embodiments, disclosed herein is a method of implanting an artificial cornea comprising: (a) providing the artificial cornea comprising an optic zone that is similar in thickness to a natural cornea and a peripheral skirt having a thickness less than the thickness of the optic zone; wherein the surface of the artificial cornea comprises one or more microstructures or nanostructures; (b) the nanometer wide lines in the peripheral skirt promotes host cell adhesion and integration; and (c) the nanopillars deter host cell adhesion and provides antimicrobial properties to the artificial cornea.

In various embodiments, disclosed herein is a kit comprising: (a) an artificial cornea; (b) composition for making microstructures and nanostructures as described herein; and (c) wherein the microstructures or nanostructures provide antimicrobial or microbicidal properties.

In various embodiments, disclosed herein is a method of treating a disease comprising: (a) an artificial cornea having microstructures or nanostructures; and (b) treating a disease with the artificial cornea.

In various embodiments, disclosed herein is a treatment regimen comprising: (a) an artificial cornea having microstructures or nanostructures; and (b) a treatment regimen that using the artificial cornea.

Throughout the disclosure, nanopillars possess a diameter and length each between 1 nm and 999 nm, and they are spaced between 1 nm and 999 nm of each other. Similarly, micropillars possess a diameter and length each between 1 µm and 999 µm, and they are spaced between 1 µm and 999 µm of each other.

In one embodiment, the corneal prosthesis described in the present disclosure would not have the drawbacks in the Boston Keratoprosthesis device, including stromal melt at the interface between materials. In one embodiment, the artificial cornea described herein is easy to implant and durable in use because the device is made from a hard polymer. In one embodiment, the micro- or nano-features on the device enables the device to have a decreased risk of bacterial infection. Additionally, in some embodiments, the use of the same polymer for both the optic zone and the skirt prevents the possibility of adhesive failure as would occur when different materials are assembled by adhesives.

Use of nano-scopic features on the surfaces of the device to direct cell response is a novel and advantageous strategy. Currently available technology in the field use either (a) a chemical coating, or tethered biomolecules, or (b) a porous or spongy microarchitecture to encourage adhesion. A chemical's coating efficacy can be diminished by various factors, such as: chemical decomposition masking of surface chemical moieties by ions and proteins naturally present in the aye; and local variations in chemical concentrations. Correct inclusions of porous microarchitectures could aid in host-cell integration; however, they are difficult to manufacture consistently. Moreover, these spongy materials are mechanically fragile, given the limited thickness of the prostheses. Importantly, there are regions of the cornea device that should be protected from overgrowth of host cells, which would reduce the transparency. No microarchitecture can perform this role and possess transparency. Moreover the features that deter host cell adhesion have also been found to be antibacterial, which is also advantageous compared to Boston K-pro Keratoprosthesis.

The present disclosure is also directed to a kit for adding a micro-structure or nano-structure coating in artificial corneas. The kit is useful for practicing the inventive method of providing the device with antimicrobial and/or microbicidal properties. The kit is an assemblage of materials or components, including at least one of the inventive compositions. Thus, in some embodiments the kit contains a composition comprising one or more elastomeric molds, polymer solution, and holders, as described above.

The exact nature of the components configured in the inventive kit depends on its intended purpose. For example, some embodiments are configured for the purpose of providing microbicidal and antimicrobial properties in an artificial cornea. In another embodiment, the kit is configured for the purposes of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to provide microstructures or nanostructures on artificial corneas. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the medical device industry and/or in the polymer industry. As used herein, the term "package" refers to a suitable solid matrix or material such as glass, plastic, paper, foil, and the like, capable of holding the individual kit components. Thus, for example, a package can be a glass vial used to contain suitable quantities of the presently disclosed inventive composition. The packaging material generally has an external label which indicates the contents and/or purpose of the kit and/or its components.

Embodiments of the present disclosure are further described in the following examples. The examples are merely illustrative and do not in any way limit the scope of the invention as claimed.

EXAMPLES

Example 1

PMMA Artificial Cornea

FIG. 1 illustrates one embodiment of the artificial cornea as described herein. The artificial cornea was made of a transparent plastic material, poly(methyl methacrylate) (PMMA). As recognized by a skilled artisan in the art, other materials could also be used, including those that are already FDA approved and known to be biocompatible. In this embodiment, the cornea has one continuous curvature on the posterior side. In one embodiment, the central part ("the optic zone"), and the peripheral part ("the peripheral skirt") may have different radii of curvature.

The polymer cornea device of FIG. 1 comprises precisely defined nano-scopic features on the surfaces of the device that can direct cell response. Specifically, the anterior and posterior surfaces of the skirt has nanometer-wide lines that promote host cell adhesion and integration, and the anterior and posterior surfaces of the optic zone has nano-meter diameter pillars that deter cell adhesion, and to prevent formation of retroprosthetic membrane and infectious keratitis. Moreover, the inventors found that the above features that deter host cell adhesion is also antibacterial, which is advantageous.

Example 2

Method of Making a Curved Patterned Surface

Figure 2:
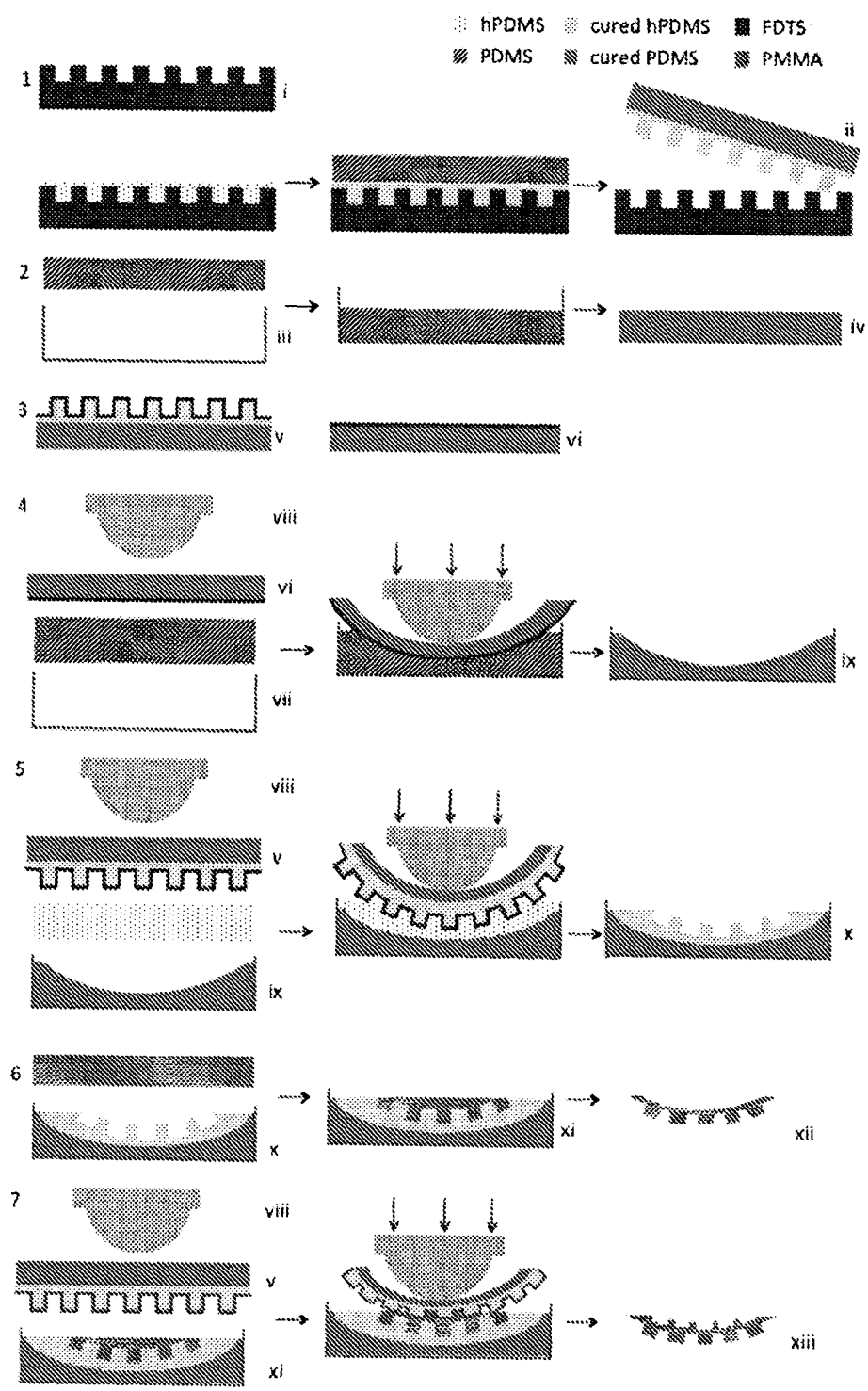
FIG. 2 illustrates, in accordance with embodiments herein, a process of making a curved nanostructured polymer surface.

FIG. 2 illustrates one embodiment of making a curved patterned surface, such as an artificial cornea as described herein. Referring to FIG. 2, in step 1, a hard mold (i) with nano-pillars with 300 nm periodicity was provided. The pillars were 190 nm in diameter and 300 nm in height. High modulus polydimethyl siloxane (hPDMS) was pipetted onto (i) and left at room temperature for 1.5 hours then cured at 65° C. for 0.5 hour. After the hPDMS was cured, polydimethyl siloxane (PDMS) prepolymer was poured on top and cured at 80° C. for one hour. After PDMS was cured, the planar silicone mold (ii) was demolded. As would be readily known to a skilled artisan, the periodicity, height, and diameter of the nanopillars can be changed by changing the mold.

In step 2 of FIG. 2, PDMS was poured in glass container (iii) and cured at 80° C. for one hour. The PDMS sheet (iv) was then peeled off from the glass container (iii). In step 3, the silicone mold (ii) and the PDMS sheet (iv) were coated with perfluorodecyltrichlorosilane (FDTS) using Molecular Vapor Deposition (MVD) to form (v) and (vi). The MVD process formed a uniform thin film of FDTS on the substrate by depositing molecules at low temperature. The FDTS monolayer reduces surface energy. FDTS is an anti-sticking precursor used to prevent adhesion between coated items with another material.

In step 4 of FIG. 2, PDMS solution was pipetted into a smaller glass container (vii). The FDTS coated PDMS sheet (vi) was pressed into the PDMS solution in the glass container (vii) with a tool (viii), with the FDTS coated side contacting PDMS, to produce a concave surface. The tool used in this procedure had a diameter of 1.5 cm with a radius of curvature of 0.69 cm. It was then cured at 80° C. for one hour and afterwards demolded. (ix) was made to be the holder for transferring the pattern and also for controlling the surface contour. As would be readily known to a skilled artisan, the thickness and radius of curvature can be easily changed, and the present disclosure is in no way limited to the specific radii and thickness disclosed herein.

In step 5 of FIG. 2, hPDMS was pipetted into (ix). (v) was pressed with the tool (viii) and left at room temperature for 1.5 hours for the hPDMS to fill the features, then cured at 65° C. for 0.5 hour. The pattern was transferred onto the concave surface after cooling and demolded. (x) was the non-planar silicone mold.

In step 6 of FIG. 2, poly-methylmethacrylate (PMMA) solution was pipetted into (x) and placed under vacuum to remove air bubbles. After the toluene had evaporated, the PMMA lens (xii) was peeled off from (xi). Using photo-polymerization to form a cross-linked PMMA lens helped in controlling the durability and thickness of the device. Finally, in step 7, (viii) was used to press (v) onto (xi). The lens (xiii) had nano-patterns on both sides after the solvent had evaporated.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. An artificial cornea, configured to be integrated into a host corneal tissue, wherein the host corneal tissue comprises a plurality of host cells, comprising:
   an optic zone having an optic zone thickness between 50 µm and 2 mm, and an anterior and a posterior optic zone surfaces; and a peripheral skirt having a skirt thickness less than the optic zone thickness, and an anterior and a posterior skirt surfaces;

wherein at least one of the anterior and the posterior optic zone surfaces comprises a plurality of micro- or nano-pillars characterized by a pillar diameter, such that the plurality of micro- or nano-pillars has antimicrobial or microbicidal properties; and or the plurality of micro- or nano-pillars deters adhesion of the plurality of host cells;

and at least one of the anterior and the posterior skirt surfaces comprises a plurality of micro- or nano-line structures characterized by a line width, such that the plurality of micro- or nano-line structures promotes adhesion of the plurality of host cells.

2. The artificial cornea of claim 1, wherein the peripheral skirt is tapered and is sutured into the host corneal tissue.

3. The artificial cornea of claim 1, wherein the artificial cornea has a posterior side characterized by a continuous curvature.

4. The artificial cornea of claim 1, wherein the artificial cornea comprises a biocompatible material.

5. The artificial cornea of claim 1, wherein the artificial cornea comprises a transparent plastic material.

6. The artificial cornea of claim 5, wherein the transparent plastic material is poly(methyl methacrylate).

7. The artificial cornea of claim 5, wherein the artificial cornea further comprises a coating selected from the group consisting of: metal oxides, fibronectin, laminin, collagen, silane, and any combination thereof.

8. The artificial cornea of claim 1, wherein the optic zone and the peripheral skirt have the same radius of curvature.

9. The artificial cornea of claim 1, wherein the optic zone and the peripheral skirt have different radii of curvature.

10. The artificial cornea of claim 1, wherein the artificial cornea has a diameter between 8 mm and 11 mm.

11. The artificial cornea of claim 1, wherein the optic zone has a diameter between 3 mm and 6 mm.

12. The artificial cornea of claim 1, wherein the peripheral skirt comprises one or more suture openings.

13. The artificial cornea of claim 12, wherein the peripheral skirt comprises 4 to 16 suture openings.

14. The artificial cornea of claim 12, wherein the one or more suture openings each has a diameter between 0.5 mm and 2 mm.

15. The artificial cornea of claim 1, wherein the line width is between 200 nm and 2000 nm.

16. The artificial cornea of claim 1, wherein both the anterior and the posterior skirt surfaces comprise the plurality of micro- or nano-line structures.

17. The artificial cornea of claim 1, wherein the plurality of micro- or nano-line structures are oriented to promote adhesion of the plurality of host cells.

18. The artificial cornea of claim 1, wherein the pillar diameter is between 20 to 200 nm.

19. The artificial cornea of claim 1, wherein the plurality of micro- or nano-pillars are tapered at the tip and the pillar diameter is between 10 nm and 200 nm.

20. The artificial cornea of claim 1, wherein the plurality of micro- or nano-pillars are characterized by a cross-sectional shape selected from the group consisting of: a round shape, a curved shape, a rectilinear shape.

21. The artificial cornea of claim 1, wherein the anterior optic zone surface comprises the plurality of micro- or nano-pillars.

22. The artificial cornea of claim 1, wherein both the anterior and the posterior optic zone surfaces comprise the plurality of micro- or nano-pillars.

23. The artificial cornea of claim 1, wherein the plurality of micro- or nano-pillars prevents formation of retroprosthetic membrane and infectious keratitis.

24. The artificial cornea of claim 1, wherein the plurality of micro- or nano-pillars and the plurality of micro- or nano-line structures comprise the same material as the artificial cornea.

25. A method of manufacturing an artificial cornea, configured to be integrated into a host corneal tissue, wherein the host corneal tissue comprises a plurality of host cells, comprising:

providing a substrate comprising a polymeric biocompatible material, wherein the substrate is characterized by a cornea thickness between 50 μm and 2 mm, a cornea diameter between 8 mm and 11 mm, and a cornea curvature; and wherein the substrate has an anterior and a posterior substrate surfaces;

imprinting a plurality of nanostructures on at least a portion of at least one of the anterior and the posterior substrate surfaces, such that the plurality of nanostructures defines on the substrate:

an optic zone having an optic zone thickness between 50 μm and 2 mm, an optic zone diameter between 3 mm and 6 mm, and an anterior and a posterior optic zone surfaces; and a peripheral skirt having a skirt thickness less than the optic zone thickness, and an anterior and a posterior skirt surfaces;

wherein at least one of the anterior and the posterior optic zone surfaces comprises a plurality of micro- or nano-pillars, such that the plurality of micro- or nano-pillars has antimicrobial or microbicidal properties, and or the plurality of micro- or nano-pillars deters adhesion of the plurality of host cells;

and at least one of the anterior and the posterior skirt surfaces comprises a plurality of micro- or nano-line structures, such that the plurality of micro- or nano-line structures promotes adhesion of the plurality of host cells;

to manufacture the artificial cornea, wherein the peripheral skirt promotes adhesion of the plurality of host cells, and the optic zone deters adhesion of the plurality of host cells and also has antimicrobial and or microbicidal properties.

26. The method of claim 25, wherein the plurality of micro- or nano-line structures is characterized by a line width of 200 to 2000 nm.

27. The method of claim 25, wherein the plurality of micro- or nano-pillars have are characterized by a pillar diameter of 10 to 200 nm.

28. The method of claim 27, wherein the plurality of micro- or nano-pillars prevents formation of retroprosthetic membrane and/or infectious keratitis.

29. A method of treating a disease in an individual comprising:

providing an artificial cornea, configured to be integrated into a host corneal tissue, wherein the host corneal tissue comprises a plurality of host cells, comprising:

an optic zone having an optic zone thickness between 50 μm and 2 mm, and an anterior and a posterior optic zone surfaces; and a peripheral skirt having a skirt thickness less than the optic zone thickness, and an anterior and a posterior skirt surfaces;

wherein at least one of the anterior and the posterior optic zone surfaces comprises a plurality of micro- or nano-pillars, such that
  the plurality of micro- or nano-pillars has antimicrobial or microbicidal properties, and or
  the plurality of micro- or nano-pillars deters adhesion of the plurality of host cells; and
at least one of the posterior and the anterior skirt surfaces comprises a plurality of micro- or nano-line structures, such that
  the plurality of micro- or nano-line structures promotes adhesion of the plurality of host cells;
integrating the artificial cornea into the host corneal tissue; and
treating the disease in the individual with the artificial cornea.

30. The method of claim 29, wherein the disease is a corneal disease.

\* \* \* \* \*